(12) United States Patent
Upadhyay et al.

(10) Patent No.: US 6,607,750 B2
(45) Date of Patent: Aug. 19, 2003

(54) DIRECTLY COMPRESSIBLE ACETAMINOPHEN COMPOSITIONS

(75) Inventors: Ajay Hasmukhlal Upadhyay, Sayreville, NJ (US); Wayne Camarco, Hoboken, NJ (US)

(73) Assignee: Rhodia Inc., Cranbury, NJ (US)

( * ) Notice: Subject to any disclaimer, the term of this patent is extended or adjusted under 35 U.S.C. 154(b) by 0 days.

(21) Appl. No.: 09/808,374

(22) Filed: Mar. 14, 2001

(65) Prior Publication Data

US 2001/0044472 A1 Nov. 22, 2001

Related U.S. Application Data

(62) Division of application No. 09/397,356, filed on Sep. 16, 1999, now Pat. No. 6,264,983.

(51) Int. Cl.$^7$ .............................. A61K 9/16; A61K 9/20
(52) U.S. Cl. ...................... 424/464; 424/465; 424/489
(58) Field of Search .................. 424/464, 465, 424/451, 489, 490, 493, 497, 458, 459

(56) References Cited

U.S. PATENT DOCUMENTS

| | | | |
|---|---|---|---|
| 3,279,998 A | 10/1966 | Raff et al. |
| 3,400,197 A | 9/1968 | Lippmann et al. |
| 4,013,785 A | 3/1977 | Weintraub et al. |
| 4,401,665 A | 8/1983 | Sheinaus et al. |
| 4,439,453 A | 3/1984 | Vogel |
| 4,600,579 A | 7/1986 | Salpekar et al. |
| 4,631,284 A | 12/1986 | Salpekar et al. |
| 4,661,521 A | 4/1987 | Salpekar et al. |
| 4,710,519 A | 12/1987 | Finnan et al. |
| 4,757,090 A | 7/1988 | Salpekar et al. |
| 4,820,522 A | 4/1989 | Radebaugh et al. |
| 4,882,167 A | 11/1989 | Jang |
| 4,894,236 A | 1/1990 | Jang et al. |
| 4,968,509 A | 11/1990 | Radebaugh et al. |
| 4,983,399 A | 1/1991 | Maish |
| 5,037,658 A | 8/1991 | Urban et al. |
| 5,073,380 A | 12/1991 | Babu et al. |
| 5,130,140 A | 7/1992 | Urban et al. |
| 5,198,228 A | 3/1993 | Urban et al. |
| 5,370,878 A | 12/1994 | Shah |
| 5,453,281 A | 9/1995 | Whistler |
| 5,587,172 A | 12/1996 | Cherukuri et al. |
| 5,635,208 A | 6/1997 | Parekh et al. |
| 5,733,578 A | 3/1998 | Hunter et al. |
| 6,217,907 B1 | 4/2001 | Hunter et al. |

FOREIGN PATENT DOCUMENTS

| | | |
|---|---|---|
| CA | 1 271 423 | 7/1990 |
| JP | 4-4297 | 4/1992 |

*Primary Examiner*—James M. Spear

(57) ABSTRACT

Acetaminophen compositions are disclosed which are capable of being directly compressed, without addition of other components, into an tablet dosage form, and which include, based on the total weight of the dry components of the composition, from about 80 percent by weight to about 98 percent by weight acetaminophen, a fluidizing agent, a binder compound, a starch, a disintegrant and a lubricant.

8 Claims, No Drawings

DIRECTLY COMPRESSIBLE ACETAMINOPHEN COMPOSITIONS

This application is a CIP of Ser. No. 09/397,356 filed Sep. 16, 1999 now U.S. Pat. No. 6,264,983.

FIELD OF THE INVENTION

This invention relates to directly compressible acetaminophen (N-acetyl-p-aminophenol or APAP) compositions and to a process for preparing such compositions. The invention also relates to the preparation of tablets from such compositions. The invention also includes such acetaminophen granulations alone or combined with other co-active ingredients present in low quantity.

BACKGROUND OF THE INVENTION

Generally there are four methods in use in the United States for manufacture of tablets, namely direct compression, dry powder blend, pre-compressed dry powder blend and wet granulation, as explained in U.S. Pat. No. 4,439,453.

In the direct compression method, all the required tabletting ingredients (active and aids) are incorporated into a free flowing granulation which is supplied to the manufacturer of bulk tablets. The granulation requires no pre-processing or blending with additional aids in order to be tabletted. Rather, the free flowing granulation supplied to the tablet manufacturer can be charged directly to a tabletting press.

The direct compression method is a generally preferred method for a number of reasons including economical reasons. The analgesic aspirin is generally tabletted using such a direct compression method since crystalline aspirin is soft and exhibits good plasticity/elasticity when compacted into tablets.

However, because the analgesic acetaminophen has significantly different properties than aspirin, it is generally considered to be non-compressible and not readily amendable to production of directly compressible granulations thereof. Generally, the less desirable wet granulation method of tabletting has been used to tablet acetaminophen. Generally, these wet granulation processes require large amounts of excipients, e.g., from about 25 to about 40% or more by weight of excipients. That is, in contrast to aspirin, the acetaminophen crystals are hard and brittle and are easily fractured. The acetaminophen crystals have essentially no plasticity/elasticity and, therefore, have required the use of unduly large amounts of aids, lubricants and/or excipients in order to be compressible into tablets by the direct compression method.

Therefore, there is a recognized need for a direct tabletting granulated acetaminophen composition that is free flowing and capable of being directly compressible into tablets. A further need is for such a directly compressible acetaminophen granulation composition to provide a high load, for example, at least 80%, or preferably at least 90% or more, of acetaminophen active in the composition. Thus, the amount of excipients required in the compositions should be kept quite low, for example, 20% or less, preferably 10% by weight or less. In addition, the directly compressible acetaminophen composition should readily be free flowing and readily permit dry blending with other active ingredients should that be desired or required. A further need is that the directly compressible acetaminophen composition be such as to provide good flow and compressibility characteristics so as to produce tablets of acceptable content uniformity, hardness and friability, and also provide a fluid bed granulation with a characteristic rough surface morphology and a high surface area suitable for good blending potential with other co-actives.

SUMMARY OF THE INVENTION

In a first aspect, the present invention is directed to an acetaminophen composition capable of being directly compressed, without addition of other components, into a compressed dosage form, said composition comprising, based on the total weight of the dry components of the composition, from greater than 90 to about 98 percent by weight acetaminophen and further comprising a fluidizing agent, a binder compound, a disintegrant and a lubricant, said composition comprising free flowing granules, at least a portion of said granules each comprising at least one acetaminophen-rich core, said acetaminophen-rich core comprising acetaminophen and fluidizing agent and having an outer surface, and a binder-rich region supported on at least a portion of the outer surface of the acetaminophen-rich core, said binder-rich region comprising binder compound, wherein, based on the dry weight of the components of the respective acetaminophen-rich core and binder-rich region, the acetaminophen-rich core comprises a relatively higher amount of acetaminophen than the binder-rich region and the binder-rich region comprises a relatively higher amount of binder than the acetaminophen-rich core.

In another aspect, the present invention is directed to an acetaminophen composition capable of being directly compressed, without addition of other components, into a compressed dosage form, said composition comprising, based on the total weight of the dry components of the composition, from greater than 80 percent by weight to about 98 percent by weight acetaminophen and further comprising a fluidizing agent, a binder compound, a disintegrant and a lubricant, said composition comprising free flowing granules, said granules exhibiting a surface area of greater than 0.8 square meters per gram.

In another aspect, the present invention is directed to an acetaminophen composition capable of being directly compressed, without addition of other components, into a compressed dosage form, said composition comprising from 90 to about 98 percent by weight acetaminophen and further comprising a fluidizing agent, a binder compound, a disintegrant and a lubricant, said composition comprising free flowing granules wherein at least a portion of said granules are made by atomizing a binder solution onto a fluidized bed of particles of the acetaminophen and fluidizing agent.

In another aspect, the present invention is directed to an acetaminophen composition capable of being directly compressed, without addition of other components, into a compressed dosage form, said composition comprising, based on the total weight of the dry components of the composition, from greater than 95 to about 98 percent by weight acetaminophen and further comprising, a combined amount of from about 2 to less than 5 percent by weight, a binder compound, a disintegrant and a lubricant.

In another aspect, the present invention is directed to an acetaminophen-containing compressed dosage form, comprising from greater than 90 percent by weight to 98 percent by weight acetaminophen and exhibiting a initial dissolution of greater than 80% according to US Pharmacopeia test method number 711, as applied to acetaminophen.

DETAILED DESCRIPTION OF INVENTION AND PREFERRED EMBODIMENTS

In a preferred embodiment, the acetaminophen composition of the present invention comprises, based on the total weight of the dry components of the composition, from 80 to 98 percent by weight (wt %), more preferably from 91 to 98 wt % and even more preferably from 94 to 97 wt %, acetaminophen, from 0.05 to 5 wt %, more preferably from 0.1 to 3.5 wt %, and even more preferably from 0.5 to 3 wt % disintegrant, from 0.05 to 5 wt %, more preferably from 0.5 to 3.25 wt % and even more preferably from 1 to 3 wt %, binder compound, from 0 to 5 wt %, more preferably from 0 to 4 wt % and even more preferably from 0 to 2 wt %, pregelatinized starch, from 0 to 3 wt %, more preferably from 0.1 to 1.25 wt % and even more preferably from 0.2 to 1 wt %, fluidizing agent and from 0.05 to 3 wt %, more preferably from 0.1 to 2 wt % and even more preferably from 0.1 to 1 wt %, lubricant.

In a first preferred embodiment, the acetaminophen composition of the present invention comprises, based on the total weight of the dry components of the composition, from about 80 to about 95 wt %, more preferably from 87.5 to 92.5 wt %, acetaminophen, from about 1 to about 4 wt %, more from preferably 1.5 to 3.5 wt %, disintegrant, from about 0.5 to about 5.0 wt %, more preferably from 2.75 to 3.25 wt %, polyvinylpyrrolidone, from about 0.5 to about 5.0 wt %, more preferably from 2 to 4 wt %, totally pregelatinized starch, from about 0.25 to about 3.0 wt %, more preferably from 0.25 to 1.25%, fluidizing agent and from about 0.25 to about 3.0 wt %, more preferably from 0.25 to 1.25%, lubricant. The composition may, optionally, further comprise up to about 10 wt % of a co-active ingredient, based on the total weight of the dry components of the composition.

In a second preferred embodiment, the acetaminophen composition of the present invention comprises, based on the total weight of the dry components of the composition: from greater than 95 to 98 wt %, more preferably from greater than 95 to 97 wt % and even more preferably from greater than 95 to 96.5 wt %, acetaminophen, from 0.05 to less than 4.9 wt %, more preferably from 0.1 to 3 wt %, and even more preferably from 0.5 to 1.5 wt % disintegrant, from 0.05 to less than 4.9 wt %, more preferably from 0.5 to 4 wt % and even more preferably from 1 to 3 wt %, binder compound, from 0 to less than 4.85 wt %, more preferably from 0 to 3 wt % and even more preferably from 0 to 2 wt %, pregelatinized starch, from 0 to 3 wt %, more preferably from 0.1 to 2 wt % and even more preferably from 0.1 to 1 wt %, fluidizing agent and from 0.05 to 3 wt %, more preferably from 0.1 to 2 wt % and even more preferably from 0.1 to 1 wt %, lubricant. The alternative preferred embodiment of the composition of the present invention allows commercial manufacture of relatively small-sized solid acetaminophen dosage forms, such as, for example, tablets, having a high acetaminophen content. The relatively small size of such solid dosage forms offers apparent advantages with respect to patient tolerance, that is, the ease with which such dosage forms may be swallowed.

Typically, the composition of the present invention further comprises a moisture content of up to about 2 wt %.

In a preferred embodiment, the composition exhibits a particle size distribution such that such that a maximum of 30 wt % is retained on a 60 US mesh screen, a maximum of 75 wt % is retained on a 100 US mesh screen, a maximum of 95 wt % is retained on a 200 US mesh screen, and a minimum of 80 wt % is retained on a 325 US mesh screen.

The acetaminophen component of the composition of the present invention may be any particulate acetaminophen. In a preferred embodiment, the particulate acetaminophen is USP grade acetaminophen in the form of a powder having a fine particle size. Preferably, the particle size of the acetaminophen particles is sufficiently small that all of the acetaminophen particles will pass through a 200 mesh screen, even more preferably all of the acetaminophen particles will pass through a 325 mesh screen.

Any pharmaceutically acceptable compound capable of rendering the acetaminophen particles compactable is suitable as the binder compound of the composition. Suitable binder compounds are known in the art and include, for example, polyvinylpyrolidones, hydroxyalkyl cellulose derivatives such as, hyrdoxypropyl methyl cellulose, hydroxypropyl cellulose and hydroxyethyl cellulose as well as mixtures thereof. In a preferred embodiment, the binder compound comprises a polyvinylpyrrolidone. Suitable polyvinylpyrrolidone are those having a number average molecular weight of up to about 90,000. In one preferred embodiment, the polyvinylpyrrolidone has a number average molecular weight (Mw) of about 30,000 or less. Such low molecular weight polyvinylpyrrolidones impart a low viscosity to the binder solutions. As examples of grades of polyvinylpyrrolidone suitable for use in the invention, there can be mentioned PVP K30, PVP K29/32 and PVP K90.

Any pharmaceutically acceptable pregelatinized starch is suitable as the pregelatinized starches of the composition of the present invention. Suitable pregelatinized starches are known in the art and include totally pregelatinized starches and partially pregelatinized starches as well as mixtures thereof. In a preferred embodiment, the pregelatinzed starch comprises a totally pregelatinized starch, such as for example, National Starch and Chemicals Corp. pregelatinized starch products 1551.

Any pharmaceutically acceptable compound that is substantially insoluble in water but capable of swelling in water in order to accelerate the disintegration and dissolution in an aqueous medium of compressed dosage forms, e.g., tablets, formed from the composition of the present invention is suitable as the disintegrant of the composition of the present invention. Suitable disintegrants are known in the art and include, for example, crosslinked sodium carboxymethylcellulose, sodium carboxylmethyl starch (also known as sodium starch glycolate), microcrystalline cellulose, soy protein, alginic acid, crosslinked polyvinylpyrrolidone (also known as crosslinked povidone) and crosslinked sodium carboxymethylcellulose ("croscarmellose sodium") as well as mixtures thereof. Preferably, the disintegrant comprises croscarmellose sodium.

In those embodiments of the composition of the present invention that are made by a fluidized bed process, it is preferred that the composition comprise a fluidizing agent. Any pharmaceutically acceptable compound effective to help keep the powders in the fluidized state during a fluidized bed granulation process is suitable as the fluidizing agents of the composition of the present invention. Suitable fluidizing agents are known in the art. In a preferred embodiment, silicon dioxide is used as the fluidizing agent. This component is multifunctional and serves as a glidant, porosity reducer, granulation densifier and moisture scavenger, but primarily is used as a fluidization aid during fluid bed granulation.

Any pharmaceutically acceptable lubricant is suitable as the lubricant of the composition of the present invention. Suitable lubricants are known in the art and include, for example, stearic acid or mixtures of fatty acids, hydrogenated vegetable oils, triglycerides of fatty acids, metal stearates, such as for example, zinc stearate and magnesium stearate, or metal salts of fatty acid mixtures, sodium lauryl sulfate, polyethylene glycol and talc, as well as mixtures thereof. Preferably, the lubricant comprises stearic acid. In a preferred embodiment, the lubricant can be added to the second binder solution or added in a dry form to the product of the granulation process by blending therewith in a suitable blender.

In a preferred embodiment, the acetaminophen composition of the present invention is made by a fluidized bed process, wherein a binder solution or dispersion is atomized onto fluidized acetaminophen particles under typical fluidized bed conditions of temperature, air flow rate and spray nozzle parameters.

In a highly preferred embodiment, the acetaminophen composition of the present invention is made by a fluidized bed process comprising:

A (i) fluidizing and, preferably, heating, preferably to a temperature in the range of about 25° C. to about 30° C., a bed, said bed comprising acetaminophen particles and at least a portion of the fluidizing agent, in a top spray fluid bed granulator by introducing a pressurized fluidization gas, such as, for example, air or heated air, to the bed;

A (ii) spraying a binder solution from an atomizing spray gun onto the fluidized, heated bed to form granules; and A (iii) drying the granules, preferably to a moisture content of from 0.3 to 2.0 wt %, more preferably from 0.8 to 1.3 wt %.

In a preferred embodiment, the binder solution of step A(ii) comprises at least a portion, preferably the major portion or all, of the polyvinylpyrrolidone dissolved in water.

The other components of the composition of the present invention may be added as components of the bed, or, more preferably, may be dry blended with the product of the fluidized bed process.

It is believed that the single spray fluidized bed process produces granules wherein at least a portion of the granules each comprise an acetaminophen-rich core and a binder-rich region supported on the acetaminophen rich core, wherein the acetaminophen-rich core comprises acetaminophen and fluidizing agent and the binder-rich region comprises the residue of the binder solution.

In an alternative highly preferred embodiment, the granules of the present invention are prepared by a fluidized bed process comprising:

B (i) placing, as dry ingredients in a top spray fluid bed granulator, and dry blending with inert fluidization gas acetaminophen powder and at least a portion, or optionally all, of the fluidizing agent, B (ii) heating the dry blend with heated pressurized fluidization gas, such as heated air, to fluidize and heat the dry blend to a temperature preferably in the range of about 25° C. to about 30° C.;

B (iii) when the dry blend has reached the desired temperature, spraying a first binder solution of at least a portion, preferably the major portion, of the polyvinylpyrrolidone dissolved in water from an atomizing spray gun of the granulation onto the heated dry blend to commence granulation of the dry powder blend;

B (iv) drying the granulation, preferably until the granulated product rises to about 2° C. above the end product temperature;

B (v) spraying a second aqueous binder solution comprising the remaining portion of the polyvinylpyrrolidone, at least a portion of the starch, and optionally a lubricant, from an atomizing gun of the granulator onto the granulated product to further granulate and agglomerate the composition, and then B (vi) drying this further granulated product, preferably until a moisture content of 1.5 wt % or less, more preferably of from about 1.0 to 1.5 wt %, is achieved.

In a preferred embodiment, a portion, preferably a minor portion, even more preferably about 15 to 35 wt %, of the total amount of pregelatinized starch is added as a component of the dry blend of step B (i) as an intra-granular disintegrant, as well as a dry binder.

In a preferred embodiment, the disintegrant is added as a component of the dry blend in step B (i). Alternatively, the disintegrant may be dry blended with particles of binder and acetaminophen made by a fluidized bed process.

Preferably, at least about 50 wt % of the fluidizing agent is used in the initial dry charge in step B (i). Any remaining portion of the fluidizing agent not charged to the granulator in the dry charge can be blended with the product of the granulation process in a suitable blender to produce the final directly compressible composition.

In preparing the first binder solution for the multi-step process, the major portion of polyvinylpyrrolidone is dispersed and dissolved in water and heated to a temperature of about 50° C. to about 70° C., preferably to about 70° C. Heating of this binder solution before use in the granulation process provides improved spreading efficiency for coating onto the powder particles of acetaminophen to achieve good compressibility of the final product. In a preferred embodiment, a major amount of the binder compound is used in the first binder solution as a particle coating agent, generally from about 60 to about 85 wt % of the total binder compound. The remaining minor amount of the binder compound, generally about 15 to 20 wt % of the total, is used in the second binder or agglomerating solution with a major amount, generally preferably about 65–85 wt % of the pregelatinized starch. Co-actives can also be incorporated into this first binder solution to ensure good content uniformity of the low dose co-actives.

In preparing the second binder solution, the remaining portions of binder compound and pregelatinized starch are dispersed in sufficient water and the solution heated, preferably to a temperature of from about 50° C. to about 70° C., more preferably to about 70° C., to insure total gelatinization of the starch granules, as well as producing efficient spreading of the second binder solution on the granulation. Optionally, low melting fatty acid mixtures, such as stearic acid or hydrogenated vegetable oils, can be dispersed within the second binder solution. During granulation with the second binder solution, the particles agglomerate while building up particle size.

The multi-spray step fluidized bed process is effective to coat and agglomerate the particles and to prepare granules having high surface area, i.e., a surface area, as measured by BET methodology, of from about 0.8 to about 1.0 $m^2/g$, and a characteristic rough surface morphology, as indicated by photomicroscopy, suitable for good blending potential, content uniformity, tablet hardness and dissolution.

It is believed that the multi-spray step fluidized bed produces granules wherein at least a portion of the granules each comprise agglomerates of granules formed in the first spray step, that is, granules which two or more acetaminophen-rich cores in a binder-rich matrix, wherein the binder-rich matrix comprises the combined residue of the binder solutions applied in the first and second spray steps.

In each of the preferred fluidized bed processes, inert fluidization gas is provided to the apparatus at a rate adequate to maintain the particle bed in a fluidized state. High fluidization gas volume is required during fluidization of the fine particle size embodiment of the composition of the present invention. For example, in large scale manufacture of about 400 kg of granulated product, an air volume of between about 1800 to 3500 cfm is generally used. Such large fluidization gas volume keeps the particles sufficiently separated while permitting binder solution to spread on the particles in a way that keeps granule growth to a minimum, producing a finer particle size of the granulation. Preferably, a three-stage level in the fluidization gas volume is used in such a large scale manufacturing process. Initially a fluidization gas volume of about 1800 cfm is used. The gas volume is then increased to about 2500 cfm about midway through granulation step B(iii), and then increased to about 3500 cfm at the beginning of the granulation with the second binder solution step B (v). This stepwise increase in fluidization gas volume keeps the particles being granulated in a highly fluidized state to produce finer particle size of the granulated product composition, and keeps the fluidized state of granulation substantially constant even though the granule density keeps increasing from commencement to termination of the granulation process. The fluidization gas used is air heated, preferably to a temperature, of at least 40° C., preferably at least about 50° C., and will generally be heated to within the range of from about 40° C. to 80° C., depending upon other process conditions including relative humidity.

Any suitable spray rate of binder solution may be used in the process of this invention. In this previously mentioned large scale manufacturing process, a binder spray rate of from about 1700 to about 2400 g/min, preferably from about 1900 to about 2100 g/min, is used.

The dried, directly compressible acetaminophen granulation composition, including acetaminophen alone or in combination with other actives, is unloaded from the fluid bed granulator, and then can, if desired, be blended with other suitable dry ingredients in a suitable blender, to provide the directly compressible acetaminophen compositions of this invention.

Sufficient atomizing fluid (air) pressure is used in the process to maintain a small droplet size for the binder solutions, and this in turn produces finer particle size in the resulting directly compressible granulated composition.

By the process of this invention, a directly compressible acetaminophen composition can be provided that has a high loading of acetaminophen, preferably a load level of at least 90 wt % acetaminophen, and enables a tabletter to produce tablets with the same dose of acetaminophen in each tablet.

The acetaminophen granulation produced by the process of this invention can be used with low dose and other fine particle size active ingredients in tablets, such as for example, with psuedoephedrine hydrochloride, chlorpheniramine maleate, dextromethorphan hydrobromide, phenylpropanolamine hydrochloride, propoxyphen napsylate, hydrocodone, codeine phosphate and the like. The acetaminophen granulation of this invention can be blended with such other active ingredients in a simple mixing process and achieve good content uniformity of the other active ingredients in any resulting tablets formed by direct compression of the resulting blend.

The process of this invention can also incorporate other low dose co-active ingredients in the granulation charge, such as for example, those used in cough and cold medications and narcotic analgesic medications, used in amounts of up to about 10% by weight, generally from about 5 to about 10%. Co-actives of cough and cold remedies for analgesic, decongestant, antihistamine, cough suppressant combinations can include, for example, pseudoephedrine hydrochloride, dextromethorphan hydrobromide, phenylpropanolamine hydrochloride, chlorpheniramine maleate, and the like. Co-active narcotic analgesic medications can include, for example, propoxyphen napsylate, hydrocodone, codeine phosphate and the like. These co-actives can be incorporated in the granulation compositions produced by the process of this invention or can be blended with the resulting fine particle size granulation produced according to the process of this invention and achieve directly compressible granulation product having good content uniformity of the active ingredients.

Optionally, other pharmaceutically acceptable excipients and additives, such as, for example surfactants or preservatives, for example, propylparaben, may be added to the composition of the present invention.

The fully formulated, i.e., drum-to-hopper, directly compressible composition of the present invention is useful to make finished oral dosage forms, such as, e.g., tablets and caplets, by conventional methods. The granulation could also be used to fill capsules. In the case of tablets, the primary advantage is in the tablet size reduction possible when using a granulation that contains a higher relative amount of active acetaminophen. For example, normally a 500 mg acetaminophen tablet would weigh approximately 595 mg when manufactured from a typical directly compressible granulation containing 84% acetaminophen. The material described in the invention can contain higher amounts of acetaminophen and thus make smaller tablets. For example, making the same 500 mg tablet with a 95% acetaminophen granulation would weigh only 526 mg. Such a lowering of tablet weight also translates into a thinner, smaller tablet. Because many high dose tablets are relatively large in size, the ability to decrease the size can be very advantageous. A smaller tablet is visually more appealing and especially, easier to swallow. The invention describes a granulation containing 95% or higher content of acetaminophen that can be directly loaded into a tablet press (without the addition of other ingredients) and finished tablets can be manufactured. Such tablets contain all the ingredients required to pass the applicable US Pharmacopeia requirements, such as, for example, USP dissolution, so that they may be suitable for sale in the marketplace.

In a preferred embodiment, the acetaminophen-containing compressed dosage form of the present invention comprises from 91 to 98 wt %, even more preferably from 94 to 97 wt %, acetaminophen.

In a preferred embodiment, the acetaminophen-containing compressed dosage form of the present invention exhibits an initial dissolution of greater than or equal to 85%, more preferably greater than or equal to 90% and even more preferably, greater than or equal to 95%, according to US Pharmacopeia test method number 711, as applied to acetaminophen.

The invention is illustrated, but not limited by, the following examples.

EXAMPLE 1

A laboratory-sized batch of directly compressible, ultra fine particle sized granulation of 90% acetaminophen was produced in a WSG-5 top spray fluidized bed granulator from Glatt GmbH of Germany.

The ingredients and their amounts used in the dry charge and first and second binder solutions were as set forth in the following Table 1:

TABLE I

DRY BOWL CHARGE

| Ingredient | Amount (gm.) | % w/w |
|---|---|---|
| Acetaminophen | 6300.0 | 90.00 |
| Croscarmellose Sodium | 210.0 | 3.00 |
| Silicon Dioxide (Syloid 244FP) | 35.0 | 0.50 |
| Starch, pregelatinized | 84.5 | 1.21 |
| 1st Granulating Binder Solution | | |
| Povidone (K-30) | 175.0 | 2.50 |
| Water | 1770.0 | — |
| 2nd Granulating Binder Solution | | |
| Povidone (K-30) | 35.0 | 0.50 |
| Starch, pregelatinized | 150.0 | 2.14 |
| Stearic Acid | 10.5 | 0.15 |
| Water | 2225.0 | — |
| Grand Total (dry) | 7000.0 | 100% |

The granulating process conditions used were as follows:

| | |
|---|---|
| atomizing guns: | single head, port size 1.8 mm, located 11" above granulator bowl |
| atomizing air pressure | 3 bars |
| inlet temp. | 48–66° C. |
| product temp. | 25–29° C. |
| binder spray rate | 60 g./min. |
| process air volume | 240–1400 cfm |

The resulting granulation composition had a moisture content of 1.4%, a bulk density of 0.38 g/cc, and a flow rate of 6.7 g/sec. The particle size of the resulting granulation composition was:

| US Mesh | % Cum. Retained |
|---|---|
| 60 | 24.8 |
| 100 | 59.6 |
| 200 | 88.0 |
| 325 | 96.8 |

Directly compressible tablets from the resulting granulation composition were produced on a Manesty Betapress Series 16 (caplet tooling size 0.281"×0.687") of Manesty Machines, Ltd. of the UK. The properties of the directly compressed tablets produced were as set forth in Table 2.

TABLE 2

| Force-main (ton)/pre-(lb) | 0.5/— | 1/— | 1.5/— | 2/— | 2.5/— | 0.75/300 | 1/400 |
|---|---|---|---|---|---|---|---|
| Ejection (lb) | 70 | 90 | 90 | 90 | 90 | 80 | 90 |
| Weight (mg) | 549 | 551 | 550 | 546 | 551 | 551 | 552 |
| Hardness (SCU) | 9.6 | 16.6 | 14.2 | 13.6 | 13.3 | 12.8 | 17.0 |
| Thickness (inch) | 0.248 | 0.231 | 0.225 | 0.222 | 0.222 | 0.237 | 0.227 |
| Friability (%) | 0.49 | 0.35 | 0.69 | 0.86 | 0.78 | 0.47 | 0.33 |

EXAMPLE 2

A production-sized batch of directly compressible, ultra fine, particle sized granulation of 90% acetaminophen was produced in a GPCG-300 top spray fluidized bed granulator from Glatt GmbH of Germany.

The ingredients and their amounts used in the dry charge and first and second binder solutions were as set forth in Table 3.

TABLE 3

DRY BOWL CHARGE

| Ingredient | Amount (kg) | % w/w |
|---|---|---|
| Acetaminophen | 360.0 | 90.00 |
| Croscarmellose Sodium | 12.00 | 3.00 |
| Silicon Dioxide (Syloid 244FP) | 2.00 | 0.50 |
| Starch, pregelatinized | 4.80 | 1.20 |
| 1st Granulating Binder Solution | | |
| Povidone (K-30) | 10.00 | 2.50 |
| Water | 101.0 | — |
| 2nd Granulating Binder Solution | | |
| Povidone (K-30) | 2.00 | 0.50 |
| Starch, pregelatinized | 8.60 | 2.15 |
| Stearic Acid | 0.60 | 0.15 |
| Water | 127.0 | — |
| Grand Total (dry) | 400.00 | 100% |

The granulating conditions used were as follows:

| | |
|---|---|
| atomizing guns: | single head, port size 1.8 mm, located 34" above granulator bowl |
| Atomizing air pressure | 6 bars |
| inlet temp. | 64–71° C. |
| product temp. | 25–31° C. |
| binder spray rate | 2000–2400 g./min. |
| process air volume | 1800–3400 cfm |

The resulting granulation composition had a moisture content of 1.4%, a bulk density of 0.43 g/cc, and a flow rate of 6.8 g/sec. The particle size of the resulting granulation composition was:

| US Mesh | % Gum. Retained |
|---|---|
| 60 | 19.6 |
| 100 | 64.8 |
| 200 | 92.9 |
| 325 | 98.4 |

Directly compressible tablets from the resulting granulation composition were produced on a Manesty Betapress Series 16 as in Example 1. The properties of the directly compressed tablets produced were as set forth in Table 4.

TABLE 4

| Force-main (ton)/pre-(lb) | 0.5/- | 1/- | 1.5/- | 2/- | 2.5/- | 0.75/300 | 1/400 |
|---|---|---|---|---|---|---|---|
| Ejection (lb) | 90 | 120 | 120 | 120 | 120 | 120 | 120 |
| Weight (mg) | 553 | 554 | 556 | 555 | 556 | 555 | 556 |
| Hardness (SCU) | 10.6 | 15.9 | 17.0 | 14.2 | 13.3 | 13.8 | 16.1 |
| Thickness (inch) | 0.244 | 0.228 | 0.224 | 0.222 | 0.221 | 0.234 | 0.228 |
| Friability (%) | 0.62 | 0.41 | 0.41 | 0.49 | 0.54 | 0.51 | 0.45 |

EXAMPLE 3

Four individual production-sized batches of directly compressible, ultra fine particle sized granulations of 90% acetaminophen were produced on a GPCG-300 top spray fluidized bed granulator from Glatt GmbH. The four individual batches were then blended together in a 125 cu. ft. Gemco blender to produce a final directly compressible blend.

The ingredients and their amounts used in the dry charge and first and second binder solutions to produce each individual batch were as set forth in Table 5.

TABLE 5

DRY BOWL CHARGE

| Ingredient | Amount (kg.) | % w/w |
|---|---|---|
| Acetaminophen | 360.0 | 89.69 |
| Croscarmellose Sodium | 10.00 | 2.49 |
| Silicon Dioxide (Syloid 244FP) | 2.00 | 0.50 |
| Starch, pregelatinized | 4.80 | 1.19 |
| 1$^{st}$ Granulating Binder Solution | | |
| Povidone (K-30) | 10.00 | 2.49 |
| Water | 101.0 | — |
| 2$^{nd}$ Granulating Binder Solution | | |
| Povidone (K-30) | 2.00 | 0.50 |
| Starch, pregelatinized | 8.60 | 2.14 |
| Water | 120.0 | — |
| Subtotal (dry) | 397.4 | |
| Post Granulation Dry Additives | | |
| Silicon Dioxide (Syloid 244FP) | 1.99 | 0.50 |
| Stearic Acid | 1.99 | 0.50 |
| Grand Total | 401.38 | 100% |

The granulating process conditions used were as follows:

| atomizing guns: | single head, port size 1.8 mm, located 11" above granulator bowl |
|---|---|
| Atomizing air pressure | 6 bars |
| Inlet temp. | 58–80° C. |
| Product temp. | 23–32° C. |
| Binder spray rate | 1999–2102 g./min. |
| Process air volume | 3000 cfm |

The resulting granulation composition of the blended individual batches had a moisture content of 1.4%, a bulk density of 0.45 g/cc, and a flow rate of 5.3 g/sec. The particle size of the blended granulation composition was:

| US Mesh Size | % Cum. Retained |
|---|---|
| 60 | 7.5 |
| 100 | 33.0 |
| 200 | 74.5 |
| 325 | 94.0 |

Directly compressible tablets from the blended granulation composition were produced on a Manesty Betapress Series 16 as in Example 1. The properties of the directly compressed tablets produced were as set forth in Table 6.

TABLE 6

| Force-main (ton)/pre-(lb) | 0.5/— | 1/— | 1.5/— | 2/— | 2.5/— | 0.75/300 | 1/400 |
|---|---|---|---|---|---|---|---|
| Ejection (lb) | 20 | 30 | 30 | 30 | 30 | 25 | 30 |
| Weight (mg) | 557 | 556 | 557 | 556 | 556 | 556 | 556 |
| Hardness (SCU) | 9.6 | 14.8 | 12.0 | 12.6 | 11.9 | 12.5 | 15.6 |
| Thickness (inch) | 0.250 | 0.233 | 0.228 | 0.225 | 0.223 | 0.238 | 0.231 |
| Friability (%) | 0.63 | 0.34 | 0.83 | 0.97 | 1.01 | 0.45 | 0.41 |

EXAMPLE 4

A production-sized batch of directly compressible, ultra fine, particle sized granulation of 90.15% acetaminophen was produced in a GPCG-300 top spray fluidized bed granulator from Glatt GmbH of Germany and blended with dry additives in a 40 cu. ft. Gemco blender.

The ingredients and their amounts used in the dry charge, first and second binder solutions, and dry additives were as set forth in Table 7.

TABLE 7

| Ingredient | Amount (kg) | % w/w |
|---|---|---|
| DRY BOWL CHARGE | | |
| Acetaminophen | 360.0 | 90.15 |
| Croscarmellose Sodium | 10.00 | 2.50 |
| Silicon Dioxide (Syloid 244FP) | 1.80 | 0.45 |
| Starch, pregelatinized | 4.80 | 1.20 |
| 1st Granulating Binder Solution | | |
| Povidone (K-30) | 10.00 | 2.50 |
| Water | 101.0 | — |
| 2nd Granulating Binder Solution | | |
| Povidone (K-30) | 2.00 | 0.50 |
| Starch, pregelatinized | 8.60 | 2.14 |
| Water | 120.0 | — |
| Post Granulation Dry Additives | | |
| Silicon Dioxide (Syloid 244FP) | 0.16 | 0.04 |
| Stearic Acid | 1.99 | 0.56 |
| Grand Total | 399.35 | 100% |

The granulating conditions used were as follows:

| | |
|---|---|
| Atomizing guns: | single head, port size 1.88 mm, located 11" above granulator bowl |
| Atomizing air pressure | 5.6–5.7 bars |
| inlet temp. | 60–75° C. |
| product temp. | 30–38° C. |
| binder spray rate | 1713–1849 g./min. |
| process air volume | 1800–3500 cfm |

The resulting granulation composition had a moisture content of 1.3%, a bulk density of 0.40 g/cc, and a flow rate of 5.1 g/sec. The particle size of the resulting granulation composition was:

| US Mesh | % Cum. Retained |
|---|---|
| 60 | 11.0 |
| 100 | 51.5 |
| 200 | 89.5 |
| 325 | 98.0 |

Directly compressible tablets from the resulting granulation composition were produced on a Manesty Betapress Series 16 as in Example 1. The properties of the directly compressed tablets produced were as set forth in Table 8.

TABLE 8

| Force-main (ton)/pre-(lb) | 0.5/— | 1/— | 1.5/— | 2/— | 2.5/— | 0.75/300 | 1/400 |
|---|---|---|---|---|---|---|---|
| Ejection (lb) | 25 | 25 | 25 | 25 | 25 | 30 | 30 |
| Weight (mg) | 559 | 559 | 557 | 559 | 557 | 555 | 557 |
| Hardness (SCU) | 13.7 | 11.9 | 12.4 | 11.9 | 11.9 | 17.0 | 19.6 |
| Thickness (inch) | 0.238 | 0.230 | 0.225 | 0.223 | 0.222 | 0.229 | 0.226 |
| Friability (%) | 0.22 | 0.53 | 0.40 | 0.49 | 0.49 | 0.18 | 0.14 |

EXAMPLES 5

A laboratory-sized batch of directly compressible, ultra fine particle sized granulation of 90% acetaminophen with chlorpheniramine maleate co-active was produced in a WSG-5 top spray fluidized bed granulator from Glatt GmbH of Germany and blended with dry additives.

The ingredients and their amounts used in the dry charge, first and second binder solutions, and any additives were as set forth in the following Table 9.

TABLE 9

| Ingredient | Amount (gm.) | % w/w |
|---|---|---|
| DRY BOWL CHARGE | | |
| Acetaminophen | 6300.0 | 90.00 |
| Croscarmellose Sodium | 149.3 | 2.13 |
| Silicon Dioxide (Syloid 244FP) | 35.0 | 0.50 |
| Starch, pregelatinized | 84.5 | 1.21 |
| 1st Granulating Binder Solution | | |
| Povidone (K-29/32) | 175.0 | 2.50 |
| Chlorpheniramine Maleate | 25.7 | 0.37 |
| Water | 2030.0 | — |
| 2nd Granulating Binder Solution | | |
| Povidone (K-29/32) | 35.0 | 0.50 |
| Starch, pregelatinized | 150.0 | 2.14 |
| Water | 2225.0 | — |
| Post Granulation Dry Additives | | |
| Silicon Dioxide (Syloid 244FP) | 35.0 | 0.50 |
| Stearic Acid | 10.5 | 0.15 |
| Grand Total | 7000.0 | 100% |

The granulating process conditions used were as follows:

| | |
|---|---|
| Atomizing guns: | single head, port size 1.88 mm, located 11" above granulator bowl |
| atomizing air pressure | 3.5 bars |
| inlet temp. | 50–73° C. |
| product temp. | 25–33° C. |
| binder spray rate | 62 g./min. |
| process air volume | 240–1400 cfm |

The resulting granulation composition had a moisture content of 1.1% a bulk density of 0.39 g/cc, and a flow rate of 5.4 g/sec. The particle size of the resulting granulation composition was:

| US Mesh | % Cum. Retained |
|---|---|
| 60 | 13.6 |
| 100 | 50.0 |
| 200 | 84.4 |
| 325 | 96.8 |

Directly compressible tablets from the resulting granulation composition were produced on a Manesty Betapress Series 16 (caplet tooling size 0.281"×0.687") of Manesty Machines, Ltd. of the UK. The properties of the directly compressed tablets produced were as set forth in Table 10.

TABLE 10

| Force-main (ton)/pre-(lb) | 1/— | 1.5/— | 0.75/300 | 1/400 |
|---|---|---|---|---|
| Ejection (lb) | 120 | 120 | 120 | 120 |
| Weight (mg) | 557 | 557 | 556 | 555 |
| Hardness (SCU) | 17.4 | 19.8 | 14.3 | 17.7 |
| Thickness (inch) | 0.231 | 0.225 | 0.238 | 0.230 |
| Friability (%) | 0.49 | 0.49 | 0.50 | 0.59 |

EXAMPLE 6

A laboratory-sized batch of directly compressible, ultra fine particle sized granulation of 89.69% acetaminophen was produced in a WSG-5 top spray fluidized bed granulator from Glatt GmbH of Germany and blended with dry additives.

The ingredients and their amounts used in the dry charge, first and second binder solutions, and dry additives were as set forth in the following Table 11.

TABLE 11

| Ingredient | Amount (gm.) | % w/w |
|---|---|---|
| DRY BOWL CHARGE | | |
| Acetaminophen | 6278.3 | 89.69 |
| Crosslinked polyvinylpyrrolidone (Crospovidone) | 174.3 | 2.49 |
| Silicon Dioxide (Syloid 244FP) | 35.0 | 0.50 |
| Starch, pregelatinized | 83.3 | 1.19 |

TABLE 11-continued

| Ingredient | Amount (gm.) | % w/w |
|---|---|---|
| 1st Granulating Binder Solution | | |
| Povidone (K-29/32) | 174.3 | 2.49 |
| Water | 1760.0 | — |
| 2nd Granulating Binder Solution | | |
| Povidone (K-29/32) | 35.0 | 0.50 |
| Starch, pregelatinized | 149.8 | 2.14 |
| Water | 2090.0 | — |
| Post Granulation Dry Additives | | |
| Silicon Dioxide (Syloid 244FP) | 35.0 | 0.50 |
| Stearic Acid | 35.0 | 0.50 |
| Grand Total | 7000.0 | 100% |

The granulating process conditions used were as follows:

| | |
|---|---|
| Atomizing guns: | single head, port size 1.88 mm, located 11" above granulator bowl |
| Atomizing air pressure | 3 bars |
| Inlet temp. | 55–70° C. |
| Product temp. | 30–34° C. |
| Binder spray rate | 60 g./min. |
| Process air volume | 240–1400 cfm |

The resulting granulation composition had a moisture content of 1.4%, a bulk density of 0.37 g/cc, and a flow rate of 5.6 g/sec. The particle size of the resulting granulation composition was:

| US Mesh | % Cum. Retained |
|---|---|
| 60 | 25.2 |
| 100 | 62.8 |
| 200 | 88.4 |
| 325 | 97.6 |

Directly compressible tablets from the resulting granulation composition were produced on a Manesty Betapress Series 16 (caplet tooling size 0.281"×0.687") of Manesty Machines, Ltd. of the UK. The properties of the directly compressed tablets produced were as set forth in Table 12.

TABLE 12

| Force-main (ton)/pre-(lb) | 0.5/— | 1/— | 1.5/— | 2/— | 2.5/— | 0.75/300 | 1/400 |
|---|---|---|---|---|---|---|---|
| Ejection (lb) | 30 | 35 | 35 | 35 | 30 | 35 | 35 |
| Weight (mg) | 555 | 557 | 556 | 554 | 555 | 558 | 558 |
| Hardness (SCU) | 13.5 | 13.7 | 12.2 | 12.4 | 12.7 | 16.2 | 18.6 |
| Thickness (inch) | 0.237 | 0.228 | 0.225 | 0.224 | 0.223 | 0.230 | 0.227 |
| Friability (%) | 0.27 | 0.85 | 0.36 | 0.36 | 0.45 | 0.22 | 0.22 |

The surface area of the particles of each of the above-produced granulations of Examples 1 to 6, measured by BET methodology with more than ten points, was within the range of from about 0.80 to about 1.0 m$^2$/g.

EXAMPLE 7

The granulated composition of Example 7 consisted of the following components: 95.00 wt % acetaminophen powder, 2.25 wt % polyvinylpyrrolidone (Povidone K90), 1.45 wt % of a pre-gelatinized starch (partially pre-gelatinized corn starch), 0.75 wt % of a disintegrant (croscarmellose sodium), 0.30 wt % of a fluidizing agent (colloidal silicon dioxide) and 0.25 wt % of a lubricant (stearic acid).

The granulated composition of Example 7 was made by top spray, fluid-bed, wet granulation in a Glatt WSG-5. The bowl of the granulator was charged with 6650 parts by weight ("pbw") acetaminophen powder and 10.5 pbw colloidal silicon dioxide. A binder solution consisting of 140 pbw polyvinylpyrrolidone and 1600 pbw water was sprayed (inlet temperature: 65° C.) onto the granulator bowl contents (bed temperature: 33° C.) over a 20 minute time period through a 1×1.8 mm nozzle aperture at an atomizer pressure of 3 bars and a flap setting of 40 and then partially dried. A second binder solution consisting of 17.5 pbw polyvinylpyrrolidone, 101.5 pbw pregelatinized starch and 1800 pbw water was sprayed (inlet temperature: 65° C.) onto the bowl contents (bed temperature: 33° C.) over a 15 minute time period through a 1×1.8 mm nozzle aperture at an atomizer pressure of 2.5 bars and a flap setting of 40. The bowl contents were then dried to a target moisture content of 1.0% and screened through a 20 mesh screen. Other excipients, i.e., 52.5 pbw croscarmellose sodium, 17.5 pbw stearic acid and 10.5 pbw colloidal silicon dioxide were then incorporated by blending for 15 minutes in a V-blender to produce granulated composition of Example 7. The granulated composition of Example 7 exhibited the following physical properties set forth in Table 13 below.

TABLE 13

| | |
|---|---|
| Bulk Density (g/ml) | 0.48–0.56 |
| Carr Index | 15 |
| Flow (g/s) | 8.8 |
| (using VanKel flowmeter) | |
| Particle size (% cumulative retained on USS sieves) | |
| 12 | 0 |
| 20 | 0 |
| 40 | 61 |
| 60 | 97 |
| 80 | 100 |
| Pan | 100 |

The granulated composition of Example 7 was directly compressed into caplet shaped (0.281 inch×0.687 inch) tablets using a Manesty Beta-press at 750 tablets/min with a force feed system. Granulation moisture content at time of tableting was 0.78%. The tabletting conditions used and tablet properties are set forth below in Table 14. Initial dissolution values in Examples 7–10 were measured according to US Pharmacopeia method 711, as applied to acetaminophen, and is reported as percent dissolved within 30 minutes.

TABLE 14

| | | | | | | |
|---|---|---|---|---|---|---|
| Pre-compression (lbs.) | 0 | 0 | 0 | 300 | 400 | 800 |
| Main compression (Tons) | 0.5 | 1 | 1.5 | 2 | 1 | 2 |
| Ejection (lbs.) | 45 | 55 | 50 | 50 | 55 | 65 |
| Tablet Weight (mg) | 527 | 527 | 528 | 526 | 527 | 526 |
| Tablet Thickness ("/1000) | 230 | 222 | 218 | 224 | 220 | 211 |
| Tablet Hardness (SC) | 11 | 15 | 10 | 13 | 14 | 20 |
| Tablet Friability (%) | 0.28 | 0.29 | 0.43 | 0.33 | 0.16 | 0.24 |
| Number of capped tablets (%) | 0 | 0 | 0 | 0 | 0 | 0 |
| Initial Disintegration (sec) | — | — | — | — | 30 | — |
| Initial Dissolution (%) | — | — | — | — | 98 | — |

EXAMPLE 8

The granulated composition of Example 8 consisted of the following components: 95.00 wt % acetaminophen powder, 1.75 wt % polyvinylpyrrolidone (Povidone K90), 1.45 wt % of a pre-gelatinized starch (partially pre-gelatinized corn starch), 1.25 wt % of a disintegrant (croscarmellose sodium), 0.30 of a fluidizing agent (colloidal silicon dioxide) and 0.25 wt % of a lubricant (stearic acid).

The granulated composition of Example 8 was made by top spray, fluid-bed, wet granulation described above in Example 7, except that a flap setting of 50 was used, the first binder solution consisted of 105 pbw polyvinylpyrrolidone and 2200 pbw water, the target moisture content was 1.0–1.3%, the particles were screened through a 12 mesh screen and 87.5 pbw croscarmelose sodium were incorporated by blending to produce granulated composition of Example 8. The granulated composition of Example 8 exhibited the following physical properties set forth in Table 15 below.

TABLE 15

| | |
|---|---|
| Bulk Density (g/ml) | 0.48–0.55 |
| Flow (g/s) | 9.0 |
| (using VanKel flowmeter) | |
| Particle size (% cumulative retained on USS sieves) | |
| 12 | 0 |
| 20 | 8 |
| 40 | 42 |
| 60 | 77 |
| 80 | 92 |
| Pan | 100 |

The granulated composition of Example 8 was directly compressed into caplet shaped tablets according to the general method described above in Example 7. Granulation moisture content at time of tabletting was 1.1%. The tabletting conditions used and tablet properties are set forth below in Table 16.

TABLE 16

| Pre-compression (lbs.) | 400 | 0 | 0 | 800 |
|---|---|---|---|---|
| Main compression (Tons) | 1 | 1.5 | 2 | 2 |
| Ejection (lbs.) | 70 | 85 | 90 | 100 |
| Tablet Weight (mg) | 834 | 838 | 842 | 842 |
| Tablet Thickness ("/1000) | 276 | 270 | 267 | 265 |
| Tablet Hardness (SC) | 15 | 20 | 22 | 20 |
| Tablet Friability (%) | 0.13 | 0.16 | 0.20 | 0.15 |
| Number of capped tablets (%) | 0 | 0 | 0 | 0 |
| Initial Disintegration (sec) | — | — | — | 52 |
| Initial Dissolution (%) | — | — | — | 97 |

EXAMPLE 9

The granulated composition of Example 9 consisted of the following components: 96.00 wt % acetaminophen powder, 1.75 wt % polyvinylpyrrolidone (Povidone K90), 0.45 wt % of a pre-gelatinized starch (partially pre-gelatinized corn starch), 1.25 wt % of a disintegrant (croscarmellose sodium), 0.30 of a fluidizing agent (colloidal silicon dioxide) and 0.25 wt % of a lubricant (stearic acid).

The granulated composition of Example 9 was made by top spray, fluid-bed, wet granulation described above in Example 7, except that a flap setting of 50 was used, the first binder solution consisted of 105 pbw polyvinylpyrrolidone and 2200 pbw water, the second binder solution consisted of 17.5 pbw povidone, 31.5 partially pre-gelatinized starch and 1800 pbw water, the target moisture content was 1.0–1.3%, the particles were screened through a 12 mesh screen and 87.5 pbw croscarmelose sodium, 17.5 pbw stearic acid and 10.5 pbw colloidal silicon dioxide were incorporated by blending to produce granulated composition of Example 9. The granulated composition of Example 8 exhibited the following physical properties set forth in Table 17 below.

TABLE 17

| Bulk Density (g/ml) | 0.48–0.55 |
|---|---|
| Flow (g/s) (using Vankel flowmeter) | 8.3 |
| Particle size (% cumulative retained on USS sieves) | |
| 12 | 0 |
| 20 | 6 |
| 40 | 32 |
| 60 | 64 |
| 80 | 85 |
| Pan | 100 |

The granulated composition of Example 9 was directly compressed into caplet shaped tablets according to the general method described above in Example 7. Granulation moisture content at time of tabletting was 1.0%. The tabletting conditions used and tablet properties are set forth below in Table 18.

TABLE 18

| Pre-compression (lbs.) | 400 | 0 | 0 | 800 |
|---|---|---|---|---|
| Main compression (Tons) | 1 | 1.5 | 2 | 2 |
| Ejection (lbs.) | 70 | 85 | 90 | 100 |
| Tablet Weight (mg) | 828 | 829 | 831 | 834 |
| Tablet Thickness ("/1000) | 275 | 269 | 265 | 263 |
| Tablet Hardness (SC) | 16 | 18 | 22 | 23 |

TABLE 18-continued

| Tablet Friability (%) | 0.29 | 0.25 | 0.37 | 0.29 |
|---|---|---|---|---|
| Number of capped tablets (%) | 0 | 0 | 0 | 0 |
| Initial Disintegration (sec) | — | — | — | 46 |
| Initial Dissolution (%) | — | — | — | 99 |

EXAMPLE 10

The granulated composition of Example 10 consisted of the same components, in the same relative amounts as in Example 8.

The granulated composition of Example 10 was made by top spray, fluid-bed, wet granulation in a Glatt WSG-5. The bowl of the granulator was charged with 6650 parts by weigh ("pbw") acetaminophen powder and 10.5 pbw colloidal silicon dioxide. A binder solution consisting of 122.5 pbw polyvinylpyrrolidone, 101.5 pbw pregelatinized starch and 3400 pbw water was sprayed (inlet temperature: 65° C.) onto the granulator bowl contents (bed temperature: 33° C.) over a 35 minute time period through a 1×1.8 mm nozzle aperture at an atomizer pressure of 3 bars and a flap setting of 50 and then dried to a target moisture content of 1.0–1.3% and screened through a 12 mesh screen. Other ingredients, i.e., 87.5 pbw croscarmelose sodium, 17.5 pbw stearic acid and 10.5 pbw colloidal silicon dioxide were then incorporated by blending for 15 minutes in a V-blender to produce granulated composition of Example 10. The granulated composition of Example 10 exhibited the physical properties set forth in Table 19 below.

TABLE 19

| Bulk Density (g/ml) | 0.48–0.55 |
|---|---|
| Flow (g/s) (using VanKel fiowmeter) | 9.0 |
| Particle size (% cumulative retained on USS sieves) | |
| 12 | 0 |
| 20 | 4 |
| 40 | 42 |
| 60 | 76 |
| 80 | 92 |
| Pan | 100 |

The granulated composition of Example 10 was directly compressed into caplet shaped tablets using the general method set forth above in Example 7. Granulation moisture content at time of tabletting was 1.0%. The tabletting conditions used and tablet properties are set forth below in Table 20.

TABLE 20

| Pre-compression (lbs.) | 400 | 0 | 0 | 800 |
|---|---|---|---|---|
| Main compression (Tons) | 1 | 1.5 | 2 | 2 |
| Ejection (lbs.) | 70 | 85 | 90 | 100 |
| Tablet Weight (mg) | 844 | 840 | 839 | 841 |
| Tablet Thickness ("/1000) | 282 | 274 | 269 | 267 |
| Tablet Hardness (SO) | 16 | 20 | 20 | 26 |
| Tablet Friability (%) | 0.44 | 0.40 | 0.74 | 0.34 |
| Number of capped tablets (%) | 0 | 0 | 0 | 0 |
| Initial Disintegration (sec) | — | — | — | 33 |
| Initial Dissolution (%) | — | — | — | 102 |

With the foregoing description of the invention, those skilled in the art will appreciate that modifications may be made to the invention without departing from the spirit thereof. Therefore, it is not intended that the scope of the invention be limited to the specific embodiments illustrated and described.

What is claimed is:

1. An acetaminophen composition capable of being directly compressed into an acetaminophen tablet, said composition comprising from about 80 to about 95 wt % acetaminophen, from about 1 to about 4 wt % essentially water-insoluble tablet/capsule disintegrant, from about 0.5 to about 5.0 wt % polyvinylpyrrolidone, from about 0.5 to about 5.0 wt % totally pregelatinized starch, about 0.25 to about 3.0 wt % of a fluidizing agent, from about 0.25 to about 3.0 wt % of a lubricant, and optionally up to about 10 wt % of a co-active ingredient, the weight percents being based on the total weight of the dry components of the composition, the composition also comprising a moisture content of up to about 1.5 wt % based on the total weight of the dry components of granulation composition, wherein the composition comprises free flowing granules, said granules comprising an acetaminophen blend and a binder coating the blend, said acetaminophen blend comprising the acetaminophen, the disintegrant, a minor portion of the starch, at least a portion of the fluidizing agent and, optionally, a portion of the lubricant, and said binder comprising polyvinylpyrolidone, the remaining starch and the remaining lubricant.

2. A directly compressible acetaminophen granulation composition of claim 1 wherein the fluidizing agent is silicon dioxide, the lubricant is stearic acid, and the tablet/capsule disintegrant is selected from crosslinked sodium carboxymethyl-cellulose and crosslinked polyvinylpyrrolidone.

3. A directly compressible acetaminophen granulation composition of claim 1 wherein the acetaminophen comprises at least about 90% by weight.

4. A directly compressible acetaminophen granulation composition of claim 1 wherein the acetaminophen comprises greater than 90% by weight.

5. A directly compressible acetaminophen granulation composition of claim 1 wherein the acetaminophen is finely divided particles of acetaminophen such that a maximum of 30 wt % is retained on a 60 US mesh screen, a maximum of 75 wt % is retained on a 100 US mesh screen, a maximum of 95 wt % is retained on a 200 US mesh screen, and a minimum of 80 wt % is retained on a 325 US mesh screen.

6. A directly compressible acetaminophen granulation composition of claim 1, wherein the acetaminophen comprises about 87.5 to about 92.5 wt %, the crosslinked sodium carboxymethylcellulose or crosslinked polyvinylpyrrolidone comprises from about 1.5 to about 3.5 wt %, the polyvinylpyrrolidone comprises from about 2.75 to about 3.25 wt %, the totally pregelatinized starch comprises from about 2.0 to about 4.0 wt %, the silicon dioxide comprises from about 0.25 to about 1.25 wt %, and the stearic acid comprises from about 0.25 to about 1.25 wt %.

7. A directly compressible acetaminophen granulation composition of claim 1 having a surface area of from about 0.8 to about 1.0 $m^2/g$.

8. A tablet comprising the granulation composition of claim 1.

* * * * *